(12) United States Patent
Gannon (10) Patent No.: US 7,052,470 B2
(45) Date of Patent: May 30, 2006

(54) BREATHING DETECTION/CONFIRMATION DEVICE

(76) Inventor: Mark D. Gannon, 2861 E. Glen Oaks Dr., Salt Lake City, UT (US) 84109

( * ) Notice: Subject to any disclaimer, the term of this patent is extended or adjusted under 35 U.S.C. 154(b) by 186 days.

(21) Appl. No.: 10/361,010

(22) Filed: Feb. 7, 2003

(65) Prior Publication Data

US 2003/0171686 A1  Sep. 11, 2003

Related U.S. Application Data

(60) Provisional application No. 60/356,306, filed on Feb. 11, 2002.

(51) Int. Cl.
 *A61B 5/08* (2006.01)
(52) U.S. Cl. ................... 600/538; 600/537; 600/529; 600/532
(58) Field of Classification Search ............ 600/529, 600/532, 533, 537, 549, 586, 382, 101, 103, 600/104, 127, 129, 131, 139, 143, 144, 160, 600/166, 178
 See application file for complete search history.

(56) References Cited

U.S. PATENT DOCUMENTS

| | | | | |
|---|---|---|---|---|
| 3,089,130 A | * | 5/1963 | Wilson | 340/575 |
| 3,241,549 A | | 3/1966 | Tyler | |
| 4,202,353 A | * | 5/1980 | Hirsch et al. | 600/537 |
| 4,475,559 A | * | 10/1984 | Horn | 600/529 |
| 4,595,016 A | * | 6/1986 | Fertig et al. | 600/532 |
| 4,648,396 A | | 3/1987 | Raemer | |
| 4,727,416 A | * | 2/1988 | Cooper et al. | 348/66 |
| 4,777,963 A | * | 10/1988 | McKenna | 600/537 |
| 4,830,022 A | * | 5/1989 | Harshe et al. | 600/537 |
| 5,063,938 A | | 11/1991 | Beck et al. | |
| 5,095,900 A | * | 3/1992 | Fertig et al. | 128/207.14 |
| 5,103,834 A | * | 4/1992 | Rineau | 600/537 |
| 5,311,875 A | | 5/1994 | Stasz | |
| 5,509,414 A | | 4/1996 | Hök | |
| 5,676,154 A | * | 10/1997 | Pettersson | 600/532 |
| 5,679,884 A | * | 10/1997 | Kirk | 73/23.3 |
| 5,797,852 A | | 8/1998 | Karakasoglu et al. | |
| 5,816,246 A | * | 10/1998 | Mirza | 600/539 |
| 5,853,005 A | | 12/1998 | Scanlon | |
| 6,017,315 A | * | 1/2000 | Starr et al. | 600/538 |
| 6,142,950 A | * | 11/2000 | Allen et al. | 600/529 |
| 6,142,951 A | * | 11/2000 | Park | 600/532 |
| 6,150,941 A | | 11/2000 | Geiger et al. | |
| 6,228,037 B1 | * | 5/2001 | Derksen | 600/529 |
| 6,368,287 B1 | * | 4/2002 | Hadas | 600/529 |
| 6,478,747 B1 | | 11/2002 | Pettersson | |

FOREIGN PATENT DOCUMENTS

EP  0 451 560 A3  10/1991
GB  2214302 A  * 8/1989

* cited by examiner

OTHER PUBLICATIONS

"Cardiopulmonary Resuscitation (CPR)", http://petplace.netscape.com/articles/artShow.asp?artID=2502, PetPlace Veterinarians, p. 1 of 3.*

*Primary Examiner*—Max Hindenburg
*Assistant Examiner*—Navin Natnithithadha
(74) *Attorney, Agent, or Firm*—Bateman IP Law Group (57) ABSTRACT

A breath detection/confirmation device includes a sensor for determining if an infant or other person is breathing, and a means for generating a human perceptible signal in response thereto. In use, the sensor is placed adjacent the infants or person's mouth/nose, and a light or some other signal indicates to the user if the infant or person is breathing.

16 Claims, 5 Drawing Sheets

BREATHING DETECTION/CONFIRMATION DEVICE

RELATED APPLICATIONS

The present application claims the benefit of U.S. Provisional Patent Application No. 60/356,306, filed Feb. 11, 2002.

BACKGROUND OF THE INVENTION

1. Field of the Invention

The present invention relates to a device for monitoring/detecting breathing. More particularly, the present invention relates to a device which may used by a person to determine if a child or other person is breathing during the night, while asleep, or following an accident.

2. State of the Art

It is common for those caring for many young children to periodically check on the child to ensure that the child is breathing. The publicity regarding sudden infant death syndrome (SIDS) and other child respiratory diseases has caused many people to be more concerned and to monitor infants more frequently.

While it is often possible to tell if an infant is breathing simply by watching for movement in his or her chest, this is often difficult to do at night. Additionally, some children will breathe so shallowly that the movements of the chest are difficult to detect. Likewise, if a child is wearing loose clothing, it may be difficult to see movement while the child breathes.

Because of this concern, many individuals will stick their hand immediately adjacent to the child's mouth/nose in an attempt to feel the child's breath. However, a sleeping infant can often breathe so softly that it is difficult to detect their breath on the skin. Additionally, smaller adults can have difficulty reaching the child's mouth/nose without touching the child if the child is sleeping in the corner of the crib.

In addition to the manual mechanism of monitoring a child's breath, there are also a large number of baby monitors which are presently available to assure a parent that a baby is alright. Such monitors include microphones which are placed in the child's crib. The microphone detects certain sound levels and often will be associated with a light array to identify the intensity of the sound. While such monitors are useful to determine if a baby is crying in a remote room, they are usually not sensitive enough to detect the breath of a sleeping infant. Additionally, the devices are often sufficiently bulky that they are not placed immediately adjacent to the child so the child will not roll over on the device.

More sophisticated monitors have been used in which a video camera provides an image of the child at some remote location. The video camera, however, is usually not sufficiently clear to observe breathing by the child. In fact, when viewing through a camera, one is usually less able to monitoring breathing than one standing adjacent a child.

Still other monitors are available in which sensors are actually placed on the infant to ensure breathing, an appropriate heart rate, etc. Such monitors, however, are undesirable in that they often include cables which can become tangled and can interfere with the free movement of the child. Additionally, the above such sensors are often expensive and can become cumbersome to use.

Thus, there is a need for an infant breathing confirmation device which allows a parent or care giver to quickly determine whether or note an infant is breathing. It would also be desirable to have such a device which facilitates placement of the device in the dark and which is easy to use without waking the child.

In addition to the above-reference scenario, there are other times in which a person may desire to detect or confirm that a person is breathing. For example, in the event of an accident, it is desirable to determine if the victim is breathing. If a person is not breathing but still alive, it is necessary to promptly begin cardiopulmonary resuscitation (CPR). This may be the case even if the person has suffered a neck or back injury. If the person is still breathing, however, it is usually desirable to avoid moving the person until trained medical help is able to evaluate the extent of the neck or back injury. If a person with neck or back trauma is improperly moved, there is a significant risk of paralysis.

Additionally, in a nursing home environment, it may be desirable to ensure that a person is breathing. Likewise, a relative of someone having sleep apnea may wish to confirm that a person is breathing while minimizing the risk of waking the person.

Thus, there is a need for a device which can be used to ensure that a person is breathing without waking or otherwise disturbing the person. Such a device should preferably be relatively inexpensive and easy to use.

SUMMARY AND OBJECT OF THE INVENTION

It is an object of the invention to provide an improved breathing detection/confirmation device which is relatively inexpensive and easy to use.

The above and other object of the invention are accomplished by a hand-held breathing/detection confirmation device configured for placing adjacent to the face of a person to determine whether the person is breathing.

In accordance with one aspect of the invention, the breath detection/confirmation device includes an elongate body which is configured so that one end of the body may be conveniently placed adjacent to the mouth/nose of an infant or other person without disturbing the person.

In accordance with another aspect of the invention, the breath detection/confirmation device includes a light to enable placement of the device adjacent to the face of the person in the dark while causing minimal disturbance to the person.

In accordance with yet another aspect of the present invention, a sensor is disposed on the device so that it is positioned adjacent to the person's face. As the sensor detects the person's breathing, it generates a human perceptible signal indicative of the person's breathing. In one embodiment of the invention, the sensor comprises a microphone which detects the sounds of the person breathing. A human perceptible signal, such as a light, provides a visual signal corresponding to the person's breathing to thereby assure that the person is breathing properly. In the alternative, a fiber optic strand or other device may be positioned so that the light breathing (such as an infant's breathing) moves the strand to thereby generate a signal corresponding with the infant's breath.

In accordance with yet another aspect of the present invention, the device is configured to maximize the likelihood that sound or breath detected by the device is from the person and not from ambient causes.

In accordance with another aspect of the invention, a variety of different sensors can be used to detect breathing without disturbing the infant or other person on whom the device is being used. It will be appreciated that various embodiments of the invention may achieve some aspects of the present invention and need not include all aspects thereof.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims. It is also to be understood that each embodiment may not accomplish each object of the invention, but provides one of more advantages over the prior art.

Figure 1:
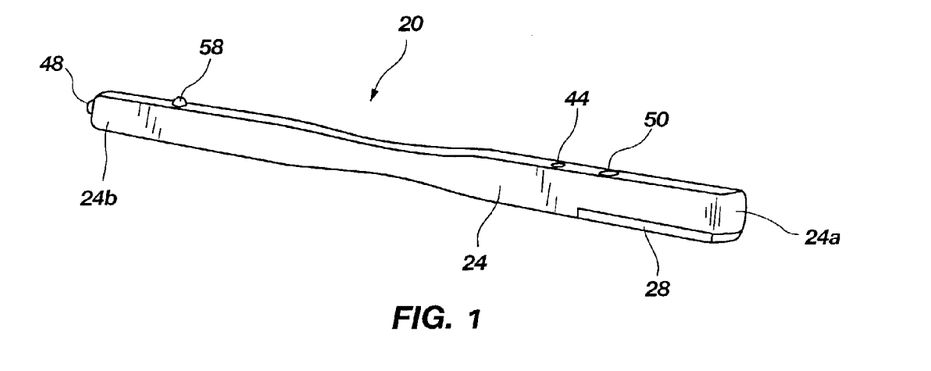
FIG. 1 shows a perspective view of a breath detection/confirmation device made in accordance with the aspects of the present invention.
Figure 2:
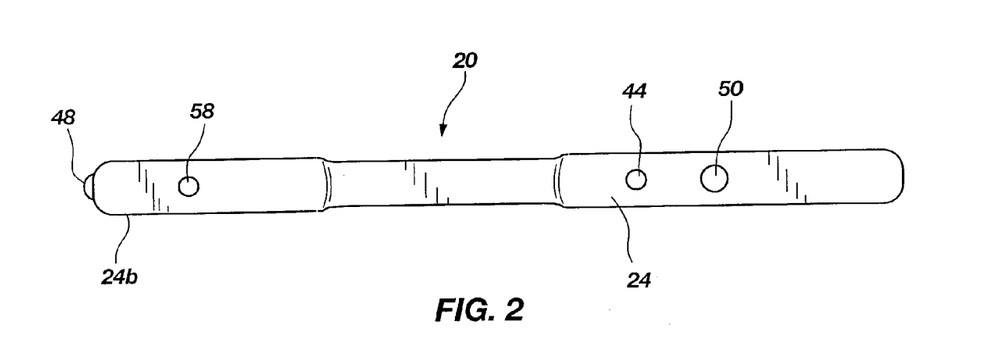
FIG. 2 shows a top view of the breath detection/confirmation device of FIG. 1.
Figure 3:
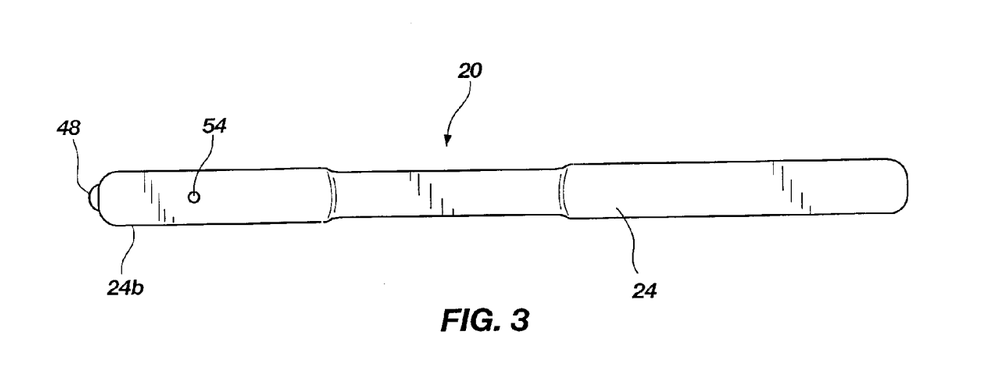
FIG. 3 shows a bottom view of the breath detection/confirmation device of FIG. 1.

Referring now to FIG. 1 through FIG. 3, there is shown a breath detection/confirmation device, generally, indicated at 20, made in accordance with one aspect of the present invention. The breath detection/confirmation device 20 includes an elongate body 24. The elongate body is preferably configured to receive a power supply. For example, the body may contain a replaceable battery compartment 28. Those skilled in the art will appreciate that numerous different power supplies, such as internal rechargeable batteries, etc. can also be used.

Disposed on a proximate handle portion 24a is a light switch 44. The light switch is disposed in communication with a light 48 on the distal portion 24b of the device. The switch 44 can be configured to turn on the light 48 as an on/off switch, or to simply illuminate the light 48, while the switch 44 is being depressed. In use, the light 48 assists the user in placing the distal end 24b of the device adjacent to the face of an infant or other person. Rather than having to turn on a light and risk waking the infant, the light 48 is strong enough to enable viewing around the face, but not so bright as to wake the infant. Thus, the light 48 allows the distal end 24b to be placed adjacent to the infant's mouth/nose without bumping the infant.

Also disposed on the proximal, handle portion is a switch 50 which is disposed in communication with a sensor 54, such a microphone disposed on the distal end of the body 24. As with the other switch, switch 50 can be configured as an on/off switch or can be configured to only actuate the sensor 54 while the switch 50 is being depressed. In use, the switches 44 and 50 are actuated so as illuminate light 48 and to actuate sensor 54. The distal end 24b of the body 24 is then placed adjacent to the infant's mouth/nose. As the infant breathes, the sensor 54 detects the breath of the infant and causes a light 58 disposed on the distal end to illuminate with each breath sensed. By seeing the flashing light, the user is able to see that the child is breathing.

Those familiar with caring for young infants will appreciate that considerable peace of mind can be obtained by periodically checking an infant to ensure that they are breathing properly. That piece of mind, however, can be somewhat disrupted if it is not apparent whether a child is breathing. By actuating the switches 44 and 50, the user is able to easily place the distal end 24b immediately adjacent to the infant's mouth/nose and to use sensor 54 to detect whether there the infant is breathing. The light 58 enlightens thereby demonstrating that the infant is breathing. Lights 48 and 58, however, are of low enough intensity that they it typically will not disturb the infant during sleep. Likewise, the device can be used with older children or adults where there is a desire to periodically check breathing without disturbing the person.

While the body 24 can be any of a variety of different shapes, it has been found that an elongate rod-like member or wand approximately 8 inches to 14 inches long is ideal. Such a length allows the user to reach a child or adult regardless of their location in the crib or on a bed, but is not so long as become cumbersome or create a risk of accidently touching the person.

Figure 4:
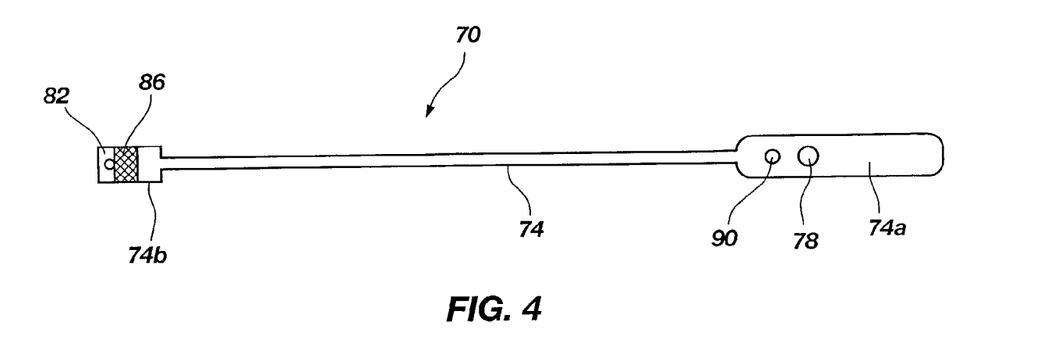
FIG. 4 shows a top view of an alternate configuration of a breath detection/confirmation device.

Turning now to FIG. 4, there is shown an alternate configuration of a breath detection/confirmation device, generally indicated at 70, made in accordance with the principles of the present invention. The breath detection/confirmation device includes an elongate body 74, which has a handle portion 74a disclosed for grasping by the user, and a distal portion 74b disposed on an opposite end thereof for disposition adjacent an infant's (or adult's) mouth/nose. The proximal end includes a switch 78 which turns on both a light 82 and a microphone 86 disposed on the distal end 74. The microphone 86 is different than sensor 54 in that the microphone extends radially about the distal end. Thus, the user need not rotate the body 74 to ensure that the speaker is disposed adjacent to the infant. Also disposed on the handle, is a means for generating a human perceptible signal in the form of a light 90. The light is disposed in communication with the microphone 86 so that the light emits visible signals when the microphone detects breathing. Those skilled in the art will appreciate that a mechanism for generating a perceptible signal could include other means such as vibration and sound. However, emitting a small flash of light is much less likely to disturb the sleep of an infant or other person.

Figure 5:
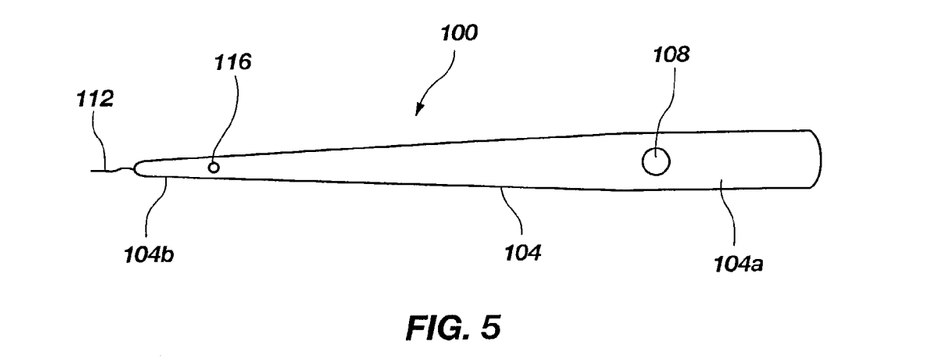
FIG. 5 shows a top view of yet another embodiment of an breath detection/confirmation device.

Turning now to FIG. 5, there is shown yet another embodiment of a breath detection/confirmation device, generally indicated at 100. The device includes a body 104 having a proximal, handle end 104a and a distal end 104b. A switch 108 is disposed on the proximal, handle portion 104a. On the opposing distal end is a vane 112 which is configured to detect breathing of an infant and a light 116 which is disposed in communication therewith to illuminate when breathing has been detected (It will be appreciated in light of the present disclosure, that the term "vane" is used herein need not be a broad member for catching the movement of air. Rather, it is meant to be any indicator which moves in the presence of a stream of air caused by breathing and is connected is such a way to generate a human perceptible signal in response to that movement.) Because the room will usually be dark, the preferred human perceptible is illumination of light 116. However, sound or vibration of the body 104 can also be used. In a preferred embodiment, the vane 112 is formed by a small thread or optical fiber which readily moves in response to breathing and is electrically or mechanically connected in such a way that movement of the thread in response to breathing generates the human perceptible signal.

While the prior art teaches a number of different baby monitors, such monitors are typically large monitors and are used to detect when the infant is crying or restless. Such monitors are generally not disposed immediately adjacent to the infant and do not detect the normal breathing of the infant while they are sleeping. The present invention, however, allows the parent to simply reach the breath detection/confirmation device so that the distal end is disposed adjacent to the infant's mouth/nose. The senor, whether it be a microphone, hair-like structure, etc., is unable to detect the infant's breath and provide a reassuring human perceptible signal assuring the parent that the infant is, in fact, breathing. While not shown in FIG. 5, the microphone or other sensor can be recessed or placed in a detent in the body to minimize detection of ambient noise.

Figure 6:
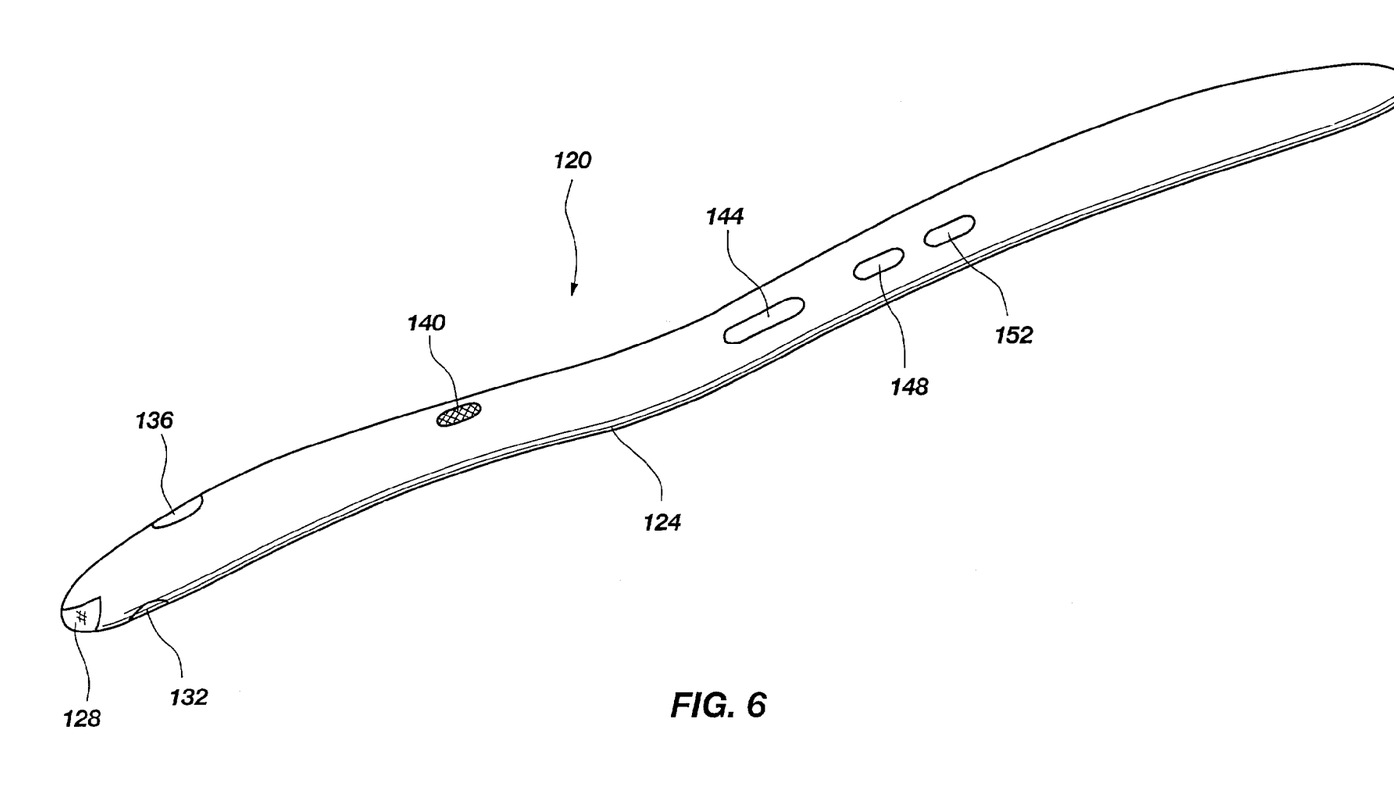
FIG. 6 shows another embodiment of a breath detection/confirmation device made in accordance with principles of the present invention.

Turning now to FIG. 6, there is shown another embodiment of a breath detection/confirmation device, generally indicated at 120, made in accordance with the principles of the present invention. The device 120 includes an elongate body 124. At a distal end 124a (i.e. away from the user) of the body 124, a locator light 128 and a breath detecting sensor 132 are positioned to facilitate placement and use of the distal end to detect whether a person is breathing. The distal end 124a of the body 124 also includes an indicator light 136 which emits a signal when sound indicates that breathing is occuring.

Disposed proximally from the distal end 124a is a speaker 140. The speaker 140 is configured for magnifying the sound sensed by the breath detector 132 so that the user can hear the breathing of the infant, etc. The speaker 140 could also be disposed more proximally if desired.

Proximally from the speaker is a volume control 144. The volume control 144 enables a user to make the speaker 140 loud enough to be heard, but not so loud as to disturb the person being monitored.

Disposed next to the volume control 144 is a detector button 148 and a locator button 152. These to buttons control the breath detector 132 and the locator light 128, respectively, to allow each to be turned on when needed, and to be turned off when not in use.

The control devices, namely the volume control 144, the detector button 148 and the locator button 152, are preferably positioned along a mid-portion of the body 124 so that they can be readily operated with the thumb or fingers of the user during use.

Figure 7:
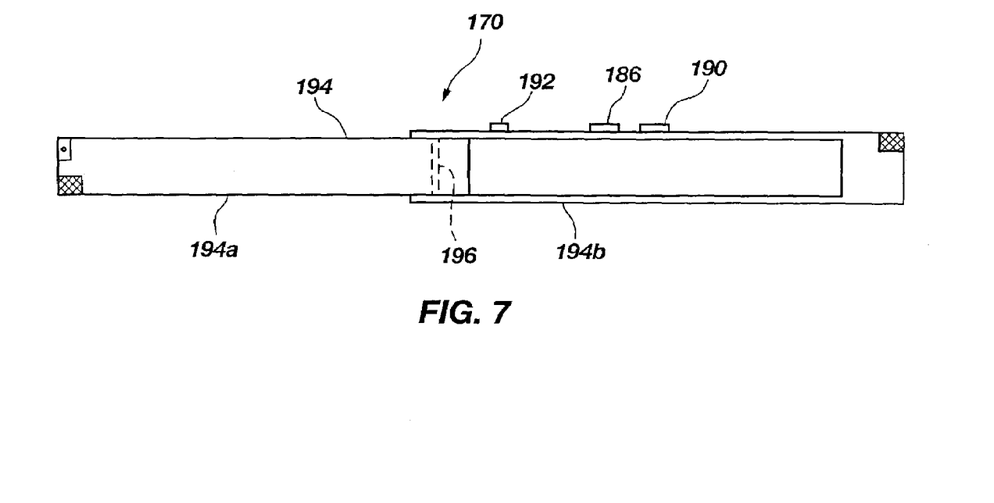
FIG. 7 shows yet another embodiment of a breath detection/confirmation device in accordance with the principles of the present invention.

Turning now to FIG. 7, there is shown an alternate embodiment of a breath detection/confirmation device, generally indicated at 170. The breath detector 170 includes a microphone 174 or other breath detecting sensor, and a locator light 178 disposed at one end. At an opposing end, a speaker 182 is provided to enable the user to hear the breathing of the infant, etc. A locator button 186 and a detector button 190 may also be provided, along with a detector light 192 for visually indicating breathing.

The breath detection/confirmation device 170 is different from the prior configurations in that the body 194 is formed in two parts 194a and 194b. The two parts 194a and 194b are attached to one another by a pin 196 or other device which enables the two parts to be folded together. Preferably, part 194a can be folded at least partially into part 194b. Thus, a twelve inch long breath detection/confirmation device 170 can be folded in half to make transport and storage more convenient. Additionally, the folding can also be used to protect the sensors from damage.

Figure 8:
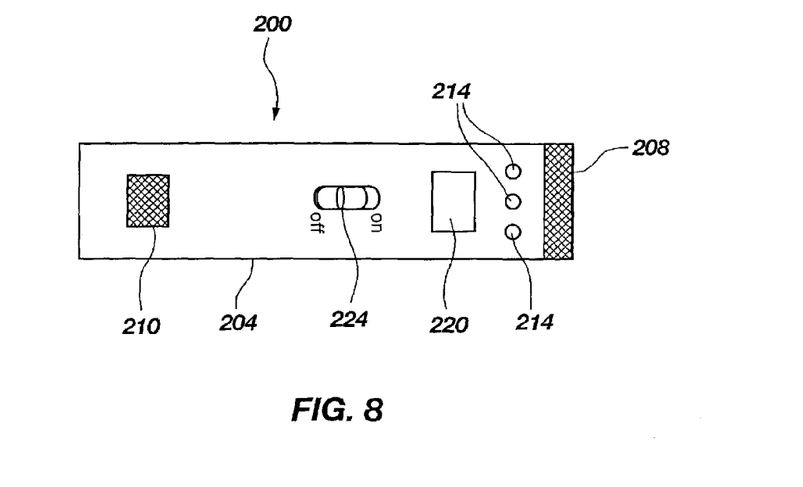
FIG. 8 shows still another embodiment of a breath detection/confirmation device in accordance with the principles of the present invention.

Turning now to FIG. 8, there is shown still another embodiment of a breath detection/confirmation device, generally indicated at 200, made in accordance with principles of the present invention. The device 200 includes a body 204 which is generally shorter and wider than that discussed with respect to the other embodiments. Because the breath detection/confirmation device 200 is generally for use in first aid kits and is intended to use with victims in accidents and the like, there is no need to prove such an elongate body. However, such a device can be used in this context if desired.

Disposed at one end of the body 204 is a microphone 208 or other sensor. A speaker 210 can be provided to amplify any sounds of breathing. Additionally, a light array 214 can be used to provide a visual indication of not only whether there is breathing, but give a visual indication of the volume or force of the breathing. Likewise, such information can be shown on a display screen 220. An on/off switch 224 can be used for selectively turning on the components of the device.

Figure 9:
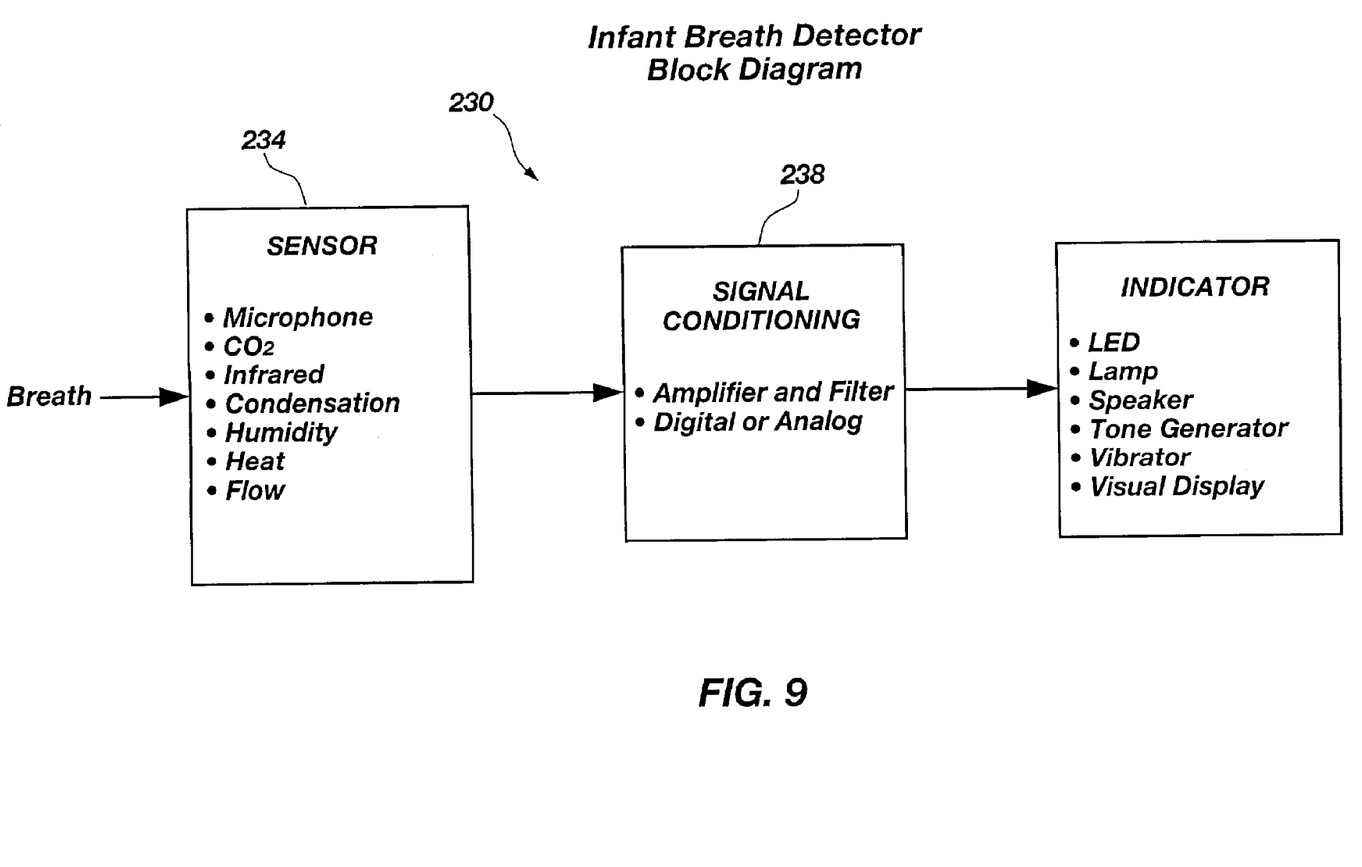
FIG. 9 shows a schematic of a breath detection/confirmation device in accordance with the principles of the present invention.

FIG. 9 shows a schematic of a Breath Detection/Confirmation Device made in accordance with the principles of the present invention. The device, generally indicated at 230, includes one or more sensors 234. As shown in FIG. 9, sensors which can be used to detect breath can include, but are not limited to, a microphone, a $CO_2$ sensor, an infrared sensor, a condensation sensor, a humidity sensor, a heat sensor and a flow sensor.

The signal(s) received from the sensor 234 can be conditioned by a variety of signal conditioning devices 238, such as amplifiers and filters. The signal(s) is then conveyed to an indicator 242. The indicators which may be used with the invention include, but are not limited to, an LED, a lamp, a speaker, a tone generator, a vibrator, a visual display and the like. Thus, a user of a breath detection/confirmation device made in accordance with principles of the present invention is able to readily determine whether an infant or other person is breathing.

Thus, there is disclosed an improved infant breathing device. It will be appreciated to those skilled in the art, in light of the present disclosure, that numerous modifications can be made. The appended claims are intended to cover such modifications.

What is claimed is:

1. A breath detection/confirmation device comprising:
    an elongate body having a proximal, handle portion, and a distal, end portion;
    the distal end portion comprising:
    a sensor detecting each breath of a person;
    a means for generating a human perceptible signal with each breath to confirm that the person is breathing; and
    a light for illuminating at least a part of a person's face allowing placement of the distal end of the device adjacent to the person's mouth or nose.

2. The breath detection/confirmation device according to claim 1, wherein the device further comprises a switch for selectively turning on the light.

3. A method for confirming the breathing of a person, the method comprising:

selecting a body having a proximal, handle end configured for holding in a human hand and a distal end, the distal end having a sensor disposed therein for confirming breathing of a person; and holding the device in the hand and positioning the device so that the distal end is disposed adjacent to the mouth or nose of a sleeping or unconscious person; and generating a human perceptible signal when the person breathes that the person is breathing; and wherein the method comprises illuminating at least a portion of the distal end of the device to facilitate placement of the distal end adjacent to the mouth or nose of the person.

4. A method according to claim 3, wherein the method comprises holding the device in the user's hand while confirming breathing.

5. A method according to claim 3, wherein the method comprises sensing breathing by use of an infrared sensor.

6. A method according to claim 3, wherein the method comprises sensing breathing by detection of condensation.

7. A method according to claim 3, wherein the method comprises sensing breathing by detection of humidity.

8. A method according to claim 3, wherein the method comprises sensing breathing by detection of heat.

9. A method according to claim 3, wherein the mehtod comprises sensing breathing by detection of fluid flow.

10. A method for confirming the breathing of a person, the method comprising:

selecting a body having a proximal, handle end configured for holding in a human hand and a distal end, the distal end having a sensor disposed therein for confirming breathing of a person; and holding the device in the hand and positioning the device so that the distal end is disposed adjacent to the mouth or nose of a sleeping or unconscious person; and generating a human perceptible signal when the person breathes that the person is breathing; and wherein the human perceptible signal comprises illuminating a light in response to each breath.

11. A method for confirming the breathing of a person, the method comprising:

selecting a body having a proximal, handle end configured for holding in a human hand and a distal end, the distal end having a sensor disposed therein for confirming breathing of a person; and holding the device in the hand and positioning the device so that the distal end is disposed adjacent to the mouth or nose of a sleeping or unconscious person; and generating a human perceptible signal when the person breathes that the person is breathing; and wherein the method comprises sensing breathing by use of a microphone.

12. A method for confirming the breathing of a person, the method comprising:

selecting a body having a proximal, handle end configured for holding in a human hand and a distal end, the distal end having a sensor disposed therein for confirming breathing of a person; and holding the device in the hand and positioning the device so that the distal end is disposed adjacent to the mouth or nose of a sleeping or unconscious person; and generating a human perceptible signal when the person breathes that the person is breathing; and wherein the method comprises sensing breathing by use of a microphone.

13. A method for confirming the breathing of a person, the method comprising:

selecting an elongate wand having a handle portion for holding in a human hand and a distal portion with a sensor disposed therein for detecting breathing, and a power supply disposed in the elongate wand for powering the sensor;

holding the elongate wand so that the distal end is disposed adjacent to the person's nose and mouth; and generating a signal in response to a breath to confirm that the person is breathing.

14. The method according to claim 13, wherein the method comprises holding the distal end adjacent to the person's nose and mouth just long enough to confirm that the person is breathing.

15. The method according to claim 13, wherein the method comprises illuminating at least a portion of the distal end of the want to assist in positioning the distal end adjacent the person's nose and mouth.

16. The method according to claim 13, wherein the method comprises illuminating a light each time the person breathes.

\* \* \* \* \*

UNITED STATES PATENT AND TRADEMARK OFFICE
CERTIFICATE OF CORRECTION

PATENT NO. : 7,052,470 B2  Page 1 of 1
APPLICATION NO. : 10/361010
DATED : May 30, 2006
INVENTOR(S) : Mark D. Gannon It is certified that error appears in the above-identified patent and that said Letters Patent is hereby corrected as shown below:

Column 1:
  Lin 15, it reads ".. which may used by a person ..."; should read --... which may be used by a person ...--
  Line 67, it reads "determine whether or note ..."; should read --determine whether or not ...--

Column 5:
  Line 52, it reads "... These to buttons control"; should read --... These two buttons control--

Column 8:
  Lines 22 and 23, it reads "... by use of a microphone."; should read --... by detecting CO2.--
  Line 42, it reads "end of the want to assist ..."; should read --end of the wand to assist ...--

Signed and Sealed this

Twenty-seventh Day of March, 2007

JON W. DUDAS
*Director of the United States Patent and Trademark Office*